US00PP16565P3

(12) United States Plant Patent
Stemkens

(10) Patent No.: US PP16,565 P3
(45) Date of Patent: May 23, 2006

(54) *GAURA* PLANT NAMED 'GAUTALWHI'

(50) Latin Name: *Gaura lindheimeri*
Varietal Denomination: Gautalwhi

(75) Inventor: Henricus G. W. Stemkens, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 242 days.

(21) Appl. No.: 10/958,040

(22) Filed: Oct. 4, 2004

(65) Prior Publication Data

US 2006/0075529 P1 Apr. 6, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—Annette H Para
(74) *Attorney, Agent, or Firm*—Edouard G. Lebel, Ph.D.

(57) ABSTRACT

A new and distinct *Gaura* plant named 'Gautalwhi', characterized by its white flowers, semi-spreading growth habit, abundant flowering and green foliage.

1 Drawing Sheet

Latin name of the genus and species of the plant claimed: *Gaura lindheimeri.*
Varietal denomination: 'Gautalwhi'.

BACKGROUND OF THE NEW PLANT

The present invention comprises a new and distinct *Gaura* plant, botanically known as *Gaura lindheimeri,* and hereinafter referred to by the cultivar name 'Gautalwhi.'

The new cultivar was developed by the inventor in a controlled breeding program during 1999, at Enkhuizen, The Netherlands. The objective of the breeding program was the development of *Gaura* cultivars with a well-branched, compact habit, continuous flowering, green foliage and early to flower.

The female (seed) parent of 'Gautalwhi' was 'A77-1', an unpatented proprietary inbredline that is not known by any synonyms. The male (pollen) parent of 'Gautalwhi' was 'A55-1', also an proprietary inbredline that is not known by any synonyms.

'Gautalwhi' was selected in May 2000 as a single flowering plant from within the F3-progeny of the above stated cross and was initially designated 'C21-4'.

Asexual reproduction of the new cultivar at Enkhuizen, The Netherlands and Sarrians, France was carried out by the use of terminal stem cuttings, and has demonstrated that the *Gaura* reproduces true to type and the characteristics as herein described are firmly fixed and retained through successive generations of such asexual propagation.

SUMMARY OF THE INVENTION

It was found that the cultivar of the present invention:

a) Exhibits white flowers;

b) Forms foliage of a green color; and c) Exhibits a semi-spreading, very well-branched growth habit.

DESCRIPTION OF THE DRAWING

This new *Gaura* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Gaura.* The data that define these characteristics were collected from asexual reproductions carried out in Enkhuizen, Netherlands. The plant history was taken on 16 weeks old plants, blossomed under natural light in a greenhouse and grown in a 13 cm container. Colour readings were taken in the greenhouse under ambient light. Colour references are primarily to The R.H.S. Colour Chart of The Royal Horticultural Society of London.

TABLE 1

Differences between the new cultivar 'Gautalwhi', its parents and a similar cultivar

| | 'Gautalwhi' | 'A77-1' | 'A55-1' | 'Wirling Butterflies' |
|---|---|---|---|---|
| Flower color | White | White | Rose | White |
| Height | 75 cm | 120 cm | 50 cm | 60 cm |
| Branching | Very good | Good | Poor | Poor |
| Flowering | Very good | Good | Poor | Good |

The plant:
Classification:
*Botanical.—Gaura.*
*Species.—Lindheimeri.*
Parentage:
*Female parent.*—A seedling named 'A77-1' is one of our seedlings from our A-generation of plants bred in 1998.

*Pollen parent.*—A seedling named 'A55-1' is one of our seedlings from our A-generation of plants bred in 1998.
Growth habit: Semi-spreading.
Plant height: 60–90 cm.
Spreading area of plant: 35–50 cm.
Strength: Very resistant to hot and cold weather.
Branching character: Freely branching and lateral branching at every node.
Blooming period: From May until November.
Propagation: Vegetative stem cuttings.
Sexuality: Hermaphrodite.
Time to initiate roots: Approximately 12 days at temperatures of 22 degrees centigrade is needed to produce rooted cuttings.
Root system: Fibrous, branching, the color is N157C.
The stem:
Diameter: 2–4 mm.
Length: 40–80 cm.
Shape: Round.
Anthocyanin pigmentation: Absent.
Color of the stem: 138C.
Length of internode: 20–60 mm, depending on the light where the plant is propagated.
Pubescence: Slightly pubescent.
The foliage:
Phyllotaxis: Alternate.
Shape of blade: Lanceolate to oblanceolate.
Attachment: Sessile.
Texture:
*Upper side.*—Slightly pubescent.
*Lower side.*—Slightly pubescent.
Venation: Pinnate.
Leaf margin: Entire to very slightly dentate.
Leaf base: Attenuate.
Leaf apex: Acute.
Length: 30–50 mm.
Width: 12–20 mm.
Depth of incision: Less than 1 mm.
Color:
*Upper side.*—146A.
*Lower side.*—146B.
Color of venation:
*Upper side.*—143B.
*Lower side.*—143B.
The bud:
Pedicel length: 3–10 mm.
Pedicel diameter: 1 mm.
Pedicel color: 141C.
Pedicel surface: Slightly hairy.
Stipule length: 1–4 mm.
Stipule width: 1–2 mm.
Stipule shape: Lanceolate.
Stipule color:
*Upper side.*—146B.
*Lower side.*—146B.
Bud size:
*Diameter.*—2 mm.
*Length.*—4–6 mm.
Bud shape: Tubular.
Bud color: From 150C with 47D veins (bottom) to 143C (top).
Bud surface: Pubescent.
Sepals:
*Color (upper side).*—N155D.
*Color (lower side).*—N155D.
*Form.*—Upright.
*Surface.*—Pubescent.
*Number.*—4, fused at tip.
*Length.*—9–14 mm.
*Width.*—2–3 mm.
*Shape.*—Tubular.
*Apex.*—Acute.
*Base.*—Subcordate.
*Margin.*—Entire.
The flower:
Type of inflorescence: Spicate raceme.
Flower shape: Single, cruciform.
Flower color:
*Upper side.*—N155A.
*Lower side.*—N155A.
Flower size:
*Height.*—20–22 mm.
*Width.*—22–26 mm.
Petals, number: 4, non-overlapping.
Petal shape: Oblanceolate.
Petal margin: Entire.
Petal apex: Acute to obtuse.
Petal base: Attenuate.
Petal length: 10–14 mm.
Petal width: 7–10 mm.
Petal texture: Smooth.
No. of flowers per inflorescence: 30–40.
Length of inflorescence (end): 25–50 cm.
Fragrance: No fragrance.
Bloom time of one inflorescence: New florets continue to open in one inflorescence over a period of 30 days.
Lastingness of one flower: 3–4 days.
Number of flowers open at one time in one inflorescence: 2–3.
Reproductive organs:
Androecium:
*Stamens quantity.*—8.
*Stamen length.*—12 mm.
*Stamen color.*—N155A.
*Anther shape.*—Elongated.
*Anther length.*—0.8 mm.
*Anther width.*—0.2 mm.
*Anther color.*—22A.
*Pollen amount.*—Plentiful pollen.
*Pollen color.*—22A.
Gynoecium:
*Pistils quantity.*—1.
*Pistil length.*—14 mm.
*Stigma color.*—4D.
*Stigma shape.*—Lobed.
*Number of lobes.*—4.
*Style color.*—N155A.
*Ovary color.*—141D.
*Ovary position.*—Inferior.
*Ovary shape.*—Elongated.
*Ovary dimensions.*—0.2 mm in width and 0.6 mm in length.
Seeds: One seed is formed per flower.
Seed size:
*Length.*—4 mm.
*Width.*—1–2 mm.
1000 seeds weight: 4.8 grams.
Seed color: 165B.
Seed texture: Smooth.
Disease resistance: Resistance to pathogens has not been observed.
Hardiness zone: 'Gautalwhi' is hardy in zones eight (8) and above.

What is claimed is:

1. A new and distinct *Gaura lindheimeri* plant named 'Gautalwhi', substantially as illustrated and described herein.

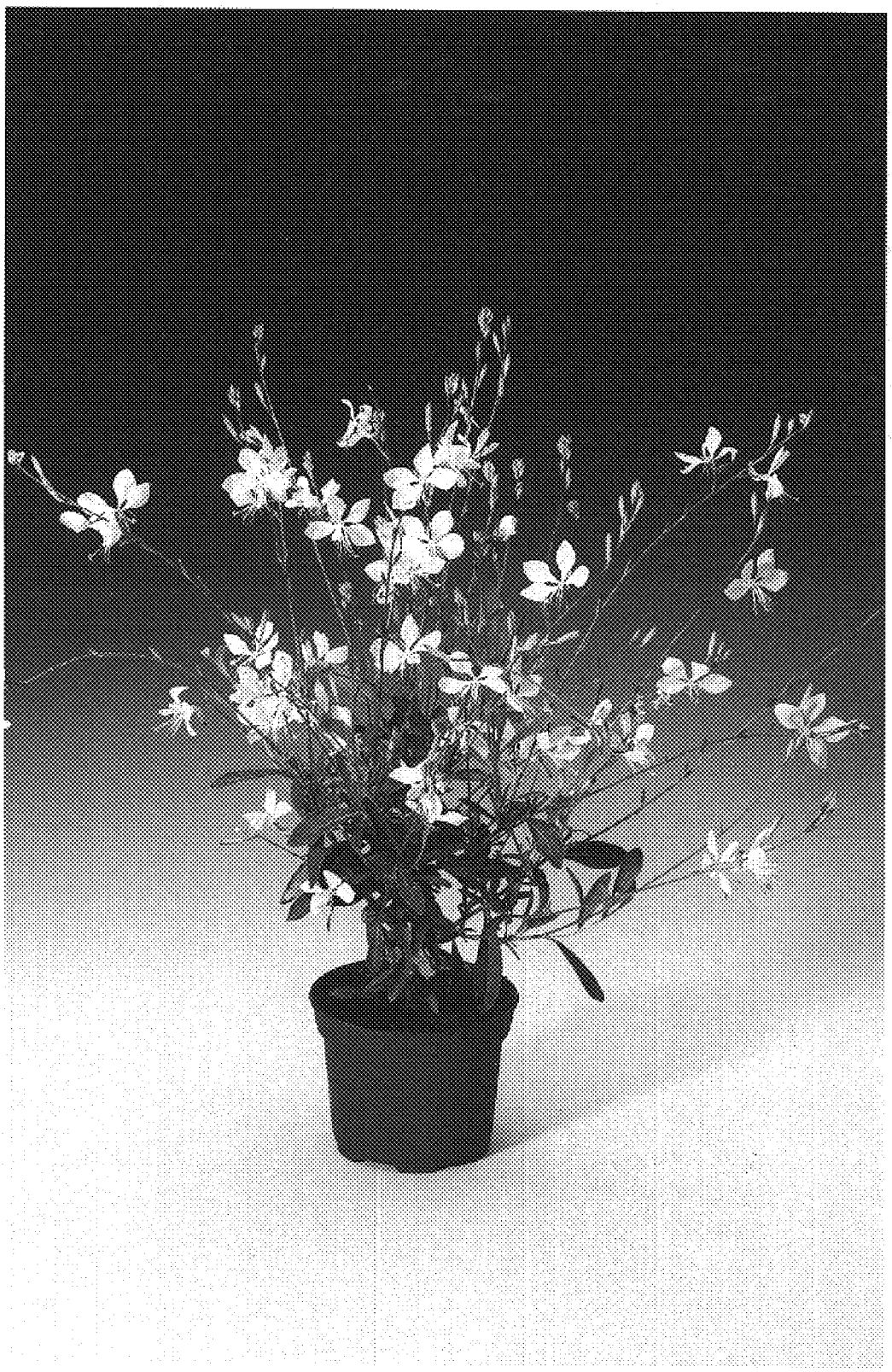

* * * * *